United States Patent [19]

Brekner et al.

[11] Patent Number: 5,087,677
[45] Date of Patent: Feb. 11, 1992

[54] PROCESS FOR THE PREPARATION OF CYCLOOLEFIN POLYMERS

[75] Inventors: Michael-Joachim Brekner, Frankfurt am Main; Jürgen Rohrmann; Walter Spaleck, both of Liederbach; Martin Antberg, Hofheim am Taunus, all of Fed. Rep. of Germany

[73] Assignee: Hoechst Aktiengesellschaft, Frankfurt am Main, Fed. Rep. of Germany

[21] Appl. No.: 548,083

[22] Filed: Jul. 5, 1990

[30] Foreign Application Priority Data

Jul. 8, 1989 [DE] Fed. Rep. of Germany ....... 3922546

[51] Int. Cl.$^5$ .............................................. C08F 4/62
[52] U.S. Cl. ................................... 526/160; 526/127; 526/132; 526/281
[58] Field of Search ............... 526/160, 281, 283, 127, 526/132, 308

[56] References Cited

U.S. PATENT DOCUMENTS

| | | | |
|---|---|---|---|
| 3,557,072 | 1/1971 | Vergne et al. | 526/281 X |
| 4,178,424 | 12/1979 | Tenney et al. | 526/283 |
| 4,948,856 | 8/1990 | Minchak et al. | 526/281 |

FOREIGN PATENT DOCUMENTS

| | | |
|---|---|---|
| 0156464 | 10/1985 | European Pat. Off. . |
| 0283164 | 9/1988 | European Pat. Off. . |
| 0291208 | 11/1988 | European Pat. Off. . |
| 0291970 | 11/1988 | European Pat. Off. . |
| 0358103 | 3/1990 | European Pat. Off. . |
| 3835044 | 4/1990 | Fed. Rep. of Germany . |

*Primary Examiner*—Fred Teskin

[57] ABSTRACT

Polymers of polycyclic olefins of the formulae I to IV having a viscosity number greater than 20 cm$^3$/g and a glass transition temperature above 100° C. are obtained without ring opening at a high polymerization rate and at polymerization temperatures advantageous from the technical point of view by means of a catalyst which is composed of a stereo-rigid, chiral metallocene compound of groups IVb to VIb of the Periodic Table of the Elements and an aluminoxane.

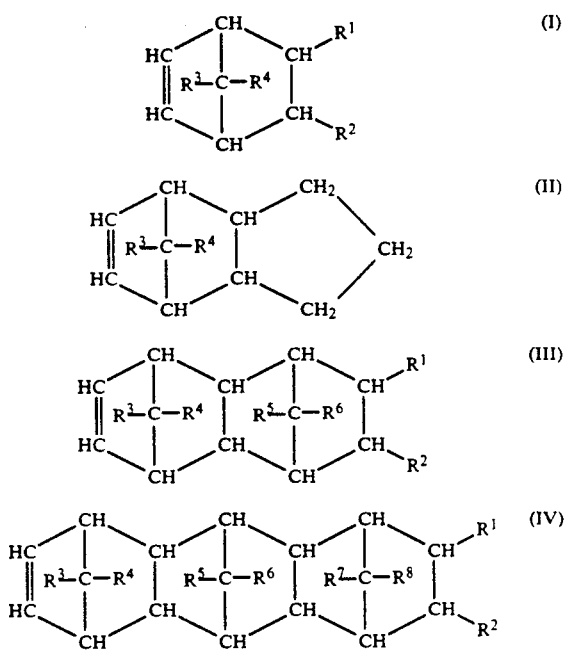

6 Claims, No Drawings

PROCESS FOR THE PREPARATION OF CYCLOOLEFIN POLYMERS

DESCRIPTION

The invention relates to a process for the preparation of homopolymers and copolymers of polycyclic olefins, in the course of which no ring opening takes place.

It is known that polycyclic olefins can be polymerized by means of various Ziegler catalysts. The polymerization takes place, depending on the catalyst, via ring-opening (cf. U.S. Pat. No. 3,557,072 and U.S. Pat. No. 4,178,424) or opening of the double bond (cf. EP 156,464, EP 283,164, EP 291,208, EP 291,970).

The disadvantage of ring-opening polymerization lies in the fact that the polymer obtained contains double bonds which can lead to chain crosslinking and hence can considerably restrict the processability of the material by extrusion or injection-molding.

In the case of cyclic olefins, polymerization with opening of the double bond results in a relatively low polymerization rate (conversion rate).

In the case of monocyclic olefins, a stereo-rigid, chiral metallocene compound, such as ethylene bis-(indenyl)-zirconium dichloride, can be used as the catalyst, polymerization taking place with retention of the ring (cf. EP 304,671).

In the case of the propylene copolymers hitherto known from the abovementioned publications, the viscosity number is less than 20 cm$^3$/g and the glass transition temperature of the copolymers of ethylene with norbornene does not exceed 100° C.

It was an object to find a process which makes it possible to obtain, in the copolymerization of polycyclic olefins with acyclic olefins, polymers having a viscosity number greater than 20 cm$^3$/g and a glass transition temperature above 100° C.

It has been found that the object can be achieved if a specific metallocene is used as the catalyst.

The invention therefore relates to a process for the preparation of a cycloolefin polymer by polymerizing 0.1 to 100% by weight, relative to the total amount of the monomers, of at least one monomer of the formulae I, II, III or IV

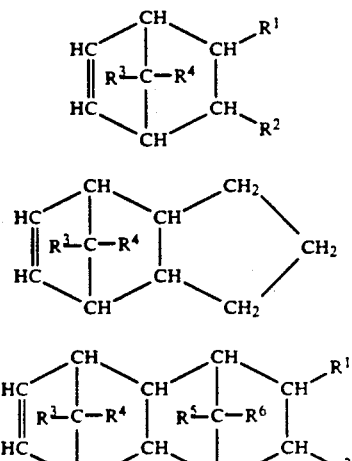

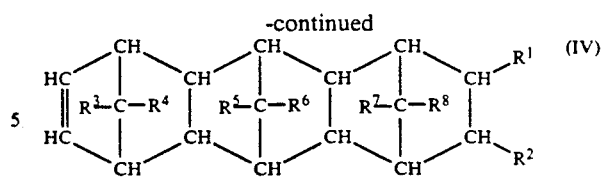

in which $R^1$, $R^2$, $R^3$, $R^4$, $R^5$, $R^6$, $R^7$ and $R^8$ are identical or different and denote a hydrogen atom or a $C_1$–$C_8$-alkyl radical, it being possible for identical radicals in the various formulae to have a different meaning, 0 to 99.9% by weight, relative to the total amount of the monomers, of a cycloolefin of the formula V

in which n is a number from 2 to 10, and 0 to 99.9% by weight, relative to the total amount of the monomers, of at least one acyclic 1-olefin of the formula VI

in which $R^9$, $R^{10}$, $R^{11}$ and $R^{12}$ are identical or different and denote a hydrogen atom or a $C_1$–$C_8$-alkyl radical, in solution, in suspension or in the gas phase, at a temperature of −78° to 150° C., under a pressure of 0.5 to 64 bar, and in the presence of a catalyst which is composed of a metallocene as the transition metal component and an aluminoxane of the formula VII

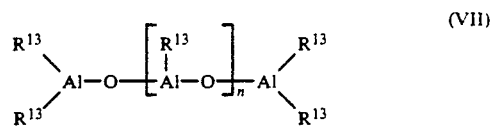

for the linear type, and/or of the formula VIII

for the cyclic type, $R^{13}$ in the formulae VII and VIII denoting a $C_1$–$C_6$-alkyl group or phenyl or benzyl and n being an integer from 2 to 50, which comprises carrying out the polymerization in the presence of a catalyst the transition metal component of which is at least one compound of the formula IX

in which
$M^1$ is titanium, zirconium, hafnium, vanadium, niobium or tantalum,
$R^{14}$ and $R^{15}$ are identical or different and denote a hydrogen atom, a halogen atom, a $C_1$–$C_{10}$-alkyl group, a $C_1$–$C_{10}$-alkoxy group, a $C_6$–$C_{10}$-aryl group, a $C_6$–$C_{10}$- aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, $R^{16}$ and $R^{17}$ are identical or different and denote a mononuclear or polynuclear hydrocarbon radical which can form a sandwich structure together with the central atom $M^1$, $R^{18}$ is

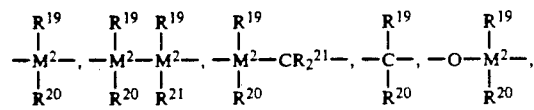

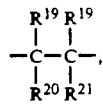

$=BR^{19}$ $=AlR^{19}$, —Ge—, —Sn—, —O—, —S—, $=SO$, $=SO_2$, $=NR^{19}$, $=CO$, $=PR^{19}$ or $=P(O)R^{19}$, $R^{19}$, $R^{20}$ and $R^{21}$ being identical or different and denoting a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{19}$ and $R^{20}$ or $R^{19}$ and $R^{21}$, in each case with the atoms linking them, forming a ring, and $M^2$ is silicon, germanium or tin.

In the process according to the invention at least one polycyclic olefin of the formulae I, II, III or IV, preferably a cycloolefin of the formula I or III

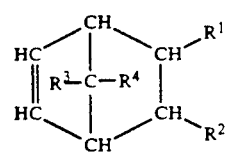

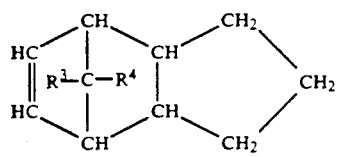

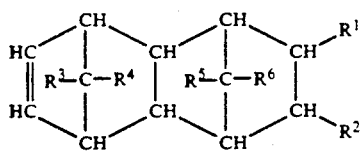

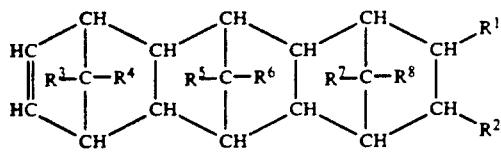

in which $R^1$, $R^2$, $R^3$, $R^4$, $R^5$, $R^6$, $R^7$ and $R^8$ are identical or different and denote a hydrogen atom or a $C_1$–$C_8$-alkyl radical, it being possible for identical radicals in the various formulae to have a different meaning, is polymerized.

If appropriate, a monocyclic olefin of the formula V

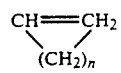

in which n is a number from 2 to 10, is also used. Another comonomer is an acyclic 1-olefin of the formula VI

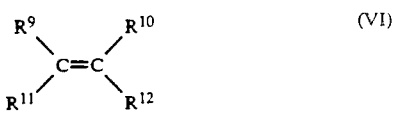

in which $R^9$, $R^{10}$, $R^{11}$ and $R^{12}$ are identical or different and denote a hydrogen atom or a $C_1$–$C_8$-alkyl radical. Ethylene or propylene is preferred.

In particular, copolymers of polycyclic olefins of the formulae I and III are prepared.

The polycyclic olefin (I to IV) is employed in an amount of 0.1 to 100% by weight, the monocyclic olefin (V) in an amount of 0 to 99.9% by weight and the acyclic 1-olefin (VI) in an amount of 0 to 99.9% by weight, in each case relative to the total amount of the monomers.

The monomers are preferably employed in the following ratios:

a) the molar ratio of polycyclic olefin (I to IV) to 1-olefin (VI as monomers is 1:99 to 99:1, preferably 20:80 to 80:20, in the corresponding polymers;

b) in the case of polymers formed from polycyclic olefins (I to IV) and monocyclic olefins (V), the molar ratio of polycyclic olefin to monocyclic olefin is 10:90 to 90:10;

c) in the case of polymers formed from polycyclic olefins (I to IV), monocyclic olefins (V) and 1-olefins (VI), the molar ratio, as monomers, of polycyclic olefin to monocyclic olefin to 1-olefin is 93:5:2 to 5:93:2 to 5:5:90, i.e. the molar ratio lies within a mixing triangle the corners of which are defined by the molar ratios 93:5:2, 5:93:2 and 5:5:90;

d) in statements a), b) and c) polycyclic olefins, monocyclic olefins and 1-olefins are to be understood as meaning also mixtures of two or more olefins of the particular type.

The catalyst to be used for the process according to the invention is composed of an aluminoxane and at least one metallocene of the formula IX

$M^1$ in formula IX is a metal from the group composed of titanium, zirconium, hafnium, vanadium, niobium and tantalum, preferably zirconium and hafnium.

$R^{13}$ and $R^{15}$ are identical or different and denote a hydrogen atom, a $C_1$–$C_{10}$-alkyl group, preferably a $C_1$–$C_3$-alkyl group, a $C_1$–$C_{10}$-alkoxy group, preferably a $C_1$–$C_3$-alkoxy group, a $C_6$–$C_{10}$-aryl group, preferably a $C_6$–$C_8$-aryl group, a $C_6$–$C_{10}$-aryloxy group, preferably a $C_6$–$C_8$-aryloxy group, a $C_2$–$C_{10}$-alkenyl group, preferably a $C_2$–$C_4$-alkenyl group, a $C_7$–$C_{40}$-arylalkyl group, preferably a $C_7$–$C_{10}$-arylalkyl group, a $C_7$–$C_{10}$-alkylaryl group, preferably a $C_7$–$C_{12}$-alkylaryl group, a $C_8$–$C_{40}$- arylalkenyl group, preferably a $C_8$–$C_{12}$-arylalkenyl group, or a halogen atom, preferably chlorine.

$R^{16}$ and $R^{17}$ are identical or different and denote a mononuclear or polynuclear hydrocarbon radical which can form a sandwich structure together with the central atom $M^1$.

$R^{16}$ and $R^{17}$ are preferably either both indenyl or tetrahydroindenyl or $R^{16}$ is fluorenyl and $R^{17}$ is cyclopentadienyl.

$R^{18}$ is a single-membered or multi-membered bridge which connects the radicals $R^{16}$ and $R^{17}$ and denotes

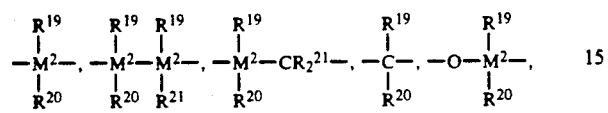

$=BR^{19}$, $=AlR^{19}$, —Ge—, —Sn—, —O—, —S—, $=SO$, $=SO_2$, $=NR^{19}$, $=CO$, $=PR^{19}$ or $=P(O)R^{19}$, $R^{19}$, $R^{20}$ and $R^{21}$ being identical or different and denoting a hydrogen atom, a halogen atom, preferably chlorine, a $C_1$–$C_{10}$-alkyl group, preferably a $C_1$–$C_3$-alkyl group, in particular a methyl group, a $C_1$–$C_{10}$-fluoroalkyl group, preferably a $CF_3$ group, a $C_6$–$C_{10}$-fluoroaryl group, preferably a pentafluorophenyl group, a $C_6$–$C_{10}$-aryl group, preferably a $C_6$–$C_8$-aryl group, a $C_1$–$C_{10}$-alkoxy group, preferably a $C_1$–$C_4$-alkoxy group, in particular a methoxy group, a $C_2$–$C_{10}$-alkenyl group, preferably a $C_2$–$C_4$-alkenyl group, a $C_7$–$C_{40}$-arylalkyl group, preferably a $C_7$–$C_{10}$-arylalkyl group, a $C_8$–$C_{40}$-arylalkenyl group, preferably a $C_8$–$C_{12}$-arylalkenyl group, or a $C_7$–$C_{40}$-alkylaryl group, preferably a $C_7$–$C_{12}$-alkylaryl group, or $R^{19}$ and $R^{20}$ or $R^{19}$ and $R^{21}$ form a ring, in each case together with the atoms linking them.

$M^2$ is silicon, germanium or tin, preferably silicon or germanium.

$R^{18}$ is preferably $=CR^{19}R^{20}$, $=SiR^{19}R^{20}$, $=GeR^{19}R^{20}$, —O—, —S—, $=SO$, $=PR^{19}$ or $=P(O)R^{19}$.

The metallocenes can be prepared in accordance with the following scheme of reactions:

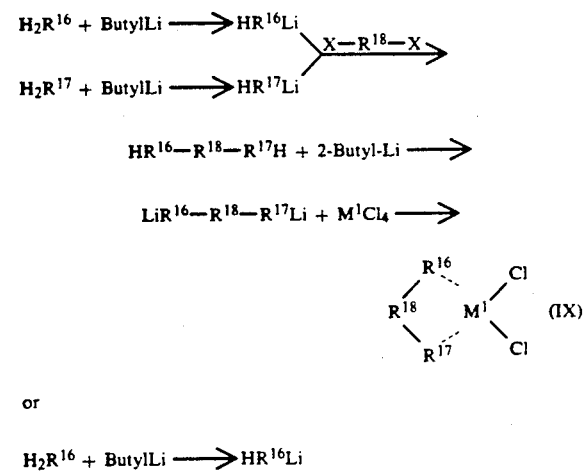

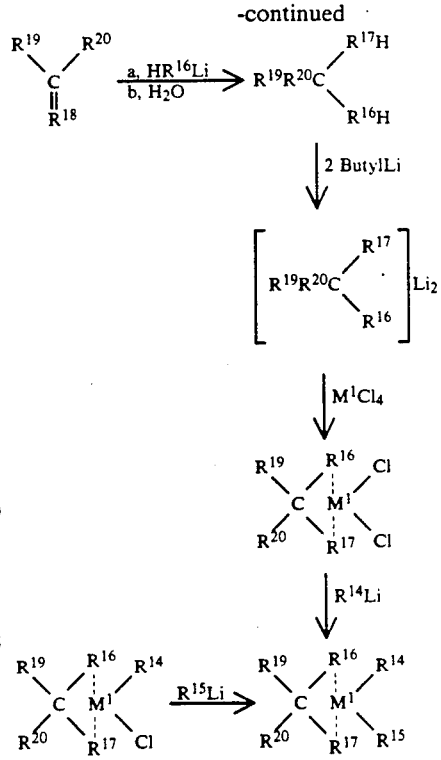

The above scheme of reactions also applies, of course, for the cases $R^{16}=R^{17}$ and/or $R^{19}=R^{20}$ and/or $R^{14}=R^{15}$.

It is preferable to employ the following metallocenes:
rac-Dimethylsilyl-bis-(1-indenyl)-zirconium dichloride,
rac-Dimethylgermyl-bis-(1-indenyl)-zirconium dichloride,
rac-Phenylmethylsilyl-bis-(1-indenyl)-zirconium dichloride,
rac-Phenylvinylsilyl-bis-(1-indenyl)-zirconium dichloride,
1-Silacyclobutyl-bis-(1'-indenyl)-zirconium dichloride,
rac-Ethylene-bis-(1-indenyl)-zirconium dichloride,
rac-Diphenylsilyl-bis-(1-indenyl)-hafnium dichloride,
rac-Phenylmethylsilyl-bis-(1-indenyl)-hafnium dichloride,
rac-Dimethylsilyl-bis-(1-indenyl)-hafnium dichloride,
rac-Diphenylsilyl-bis-(1-indenyl)-zirconium dichloride,
Diphenylmethylene-(9-fluorenyl)-cyclopentadienyl-zirconium dichloride,
Isopropylene-(9-fluorenyl)-cyclopentadienyl-zirconium dichloride or mixtures thereof.

The following are particularly preferred in this regard:
rac-Dimethylsilyl-bis-(1-indenyl)-zirconium dichloride,
rac-Phenylmethylsilyl-bis-(1-indenyl)-zirconium dichloride,
rac-Phenylvinylsilyl-bis-(1-indenyl)-zirconium dichloride,
1-Silacyclobutyl-bis-(1'-indenyl)-zirconium dichloride,
rac-Ethylene-bis-(1-indenyl)-zirconium dichloride,
rac-Diphenylsilyl-bis-(1-indenyl)-zirconium dichloride,
Diphenylmethylene-(9-fluorenyl)-cyclopentadienyl-zirconium dichloride,
Isopropylene-(9-fluorenyl)-cyclopentadienyl-zirconium dichloride or mixtures thereof.

The co-catalyst is an aluminoxane of the formula VII

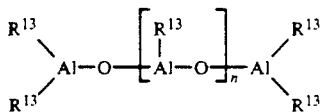

(VII)

for the linear type and/or of the formula VIII

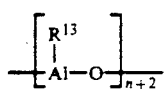

(VIII)

for the cyclic type. In these formulae $R^{13}$ denotes a $C_1$-$C_6$-alkyl group, preferably methyl, ethyl, isobutyl, butyl or neopentyl, or phenyl or benzyl. Methyl is particularly preferred. n is an integer from 2 to 50, preferably 5 to 40. The exact structure of the aluminoxane is, however, not known.

The aluminoxane can be prepared in various ways.

In one of the processes finely powdered copper sulfate pentahydrate is suspended in toluene and sufficient aluminum trialkyl for about 1 mole of $CuSO_4.5H_2O$ to be available for 4 Al atoms in each case is added in a glass flask, at about $-20°$ C. and under an inert gas. After a slow hydrolysis with the elimination of alkane, the reaction mixture is kept at room temperature for 24 to 48 hours, in the course of which it may be necessary to cool so that the temperature does not rise above $30°$ C. The copper sulfate is then filtered off from the aluminoxane dissolved in toluene, and the solution is concentrated in vacuo. It is assumed that in this process of preparation the low-molecular aluminoxanes undergo a condensation reaction to give higher oligomers with the elimination of aluminum trialkyl.

Aluminoxanes are also obtained if an aluminum trialkyl, preferably aluminum trimethyl, dissolved in an inert aliphatic or aromatic solvent, preferably heptance or toluene, is reacted with aluminum salts containing water of crystallization, preferably aluminum sulfate, at a temperature of $-20$ to $100°$ C. In this case the ratio by volume between the solvent and the aluminum alkyl used is 1:1 to 50:1—preferably 5:1—and the reaction time, which can be monitored by the elimination of the alkane, is 1 to 200 hours—preferably 10 to 40 hours.

Aluminum salts containing water of crystallization which are preferably used are those having a high content of water of crystallization. Aluminum sulfate hydrate, above all the compounds $Al_2(SO_4)_3.16H_2O$ and $Al_2(SO_4)_3.18H_2O$, which have the particularly high content of water of crystallization of 16 and 18, respectively, moles of $H_2O$/mole of $Al_2(SO_4)_3$, is particularly preferred.

Another variant for the preparation of aluminoxanes consists in dissolving an aluminum trialkyl, preferably aluminum trimethyl, in the suspending agent, previously placed in the polymerization kettle, preferably in the liquid monomer, in heptane or toluene, and then reacting the aluminum compound with water.

As well as the processes for the preparation of aluminoxanes described above, there are others which can be used. Irrespective of the mode of preparation, a factor common to all the aluminoxane solutions is a varying amount of unreacted aluminum trialkyl, which is present in free form or as an adduct. This content has an effect, which has not yet been accurately explained and which varies depending on the metallocene compound employed, on the catalytic activity.

Before it is used in the polymerization reaction, the metallocene can be pre-activated by means of an aluminoxane of the formula II and/or III. This markedly increases the polymerization activity.

The pre-activation of the transition metal compound is carried out in solution. In this process the metallocene is preferably dissolved in a solution of the aluminoxane in an inert hydrocarbon. Suitable inert hydrocarbons are aliphatic or aromatic hydrocarbons. It is preferable to use toluene.

The concentration of the aluminoxane in the solution is within the range from approx. 1% by weight up to the saturation limit, preferably from 5 to 30% by weight, in each case relative to the total solution. The metallocene can be employed in the same concentration, but it is preferably employed in an amount of $10^{-4}$-1 mole per mole of aluminoxane. The pre-activation time is 5 minutes to 60 hours, preferably 5 to 60 minutes. The reaction is carried out at a temperature of $-78°$ C. to $100°$ C., preferably $0°$ to $70°$ C.

A markedly longer pre-activation is possible, but it normally has no effect either on increasing or decreasing the activity, though it can be quite useful for storage purposes.

The polymerization is carried out in an inert solvent customary for the Ziegler low-pressure process, for example in an aliphatic or cycloaliphatic hydrocarbon; examples of these which may be mentioned are butane, pentane, hexane, heptane, isooctane, cyclohexane and methylcyclohexane. It is also possible to use a gasoline or hydrogenated diesel oil fraction which has been carefully freed from oxygen, sulfur compounds and moisture. Toluene can also be used.

Finally, the monomer to be polymerized can also be used as the solvent or suspending agent. In the case of norbornene, bulk polymerizations of this type are carried out at a temperature above $45°$ C. The molecular weight of the polymer can be regulated in a known manner; it is preferable to use hydrogen for this purpose.

The polymerization is carried out in a known manner in solution, in suspension or in the gas phase, continuously or discontinuously, in a single stage or in several stages and at a temperature of $-78°$ to $150°$ C., preferably $20°$ to $80°$ C. The pressure is 0.5 to 64 bar and is maintained either by mean of the gaseous olefins or by means of an inert gas.

Continuous and multi-stage processes are particularly advantageous, because they make it possible to use the polycyclic olefin in an efficient manner. In continuous processes it also possible to recover the polycyclic olefin, which can be obtained in the form of residual monomer together with the polymer, and to recycle it to the reaction mixture.

In this reaction the metallocene compound is used in a concentration, relative to the transition metal, of $10^{-3}$ to $10^{-7}$, preferably $10^{-5}$ to $10^{-6}$, mole of transition metal per $dm^3$ of reactor volume. The aluminoxane is used in a concentration of $10^{-4}$ to $10^{-1}$, preferably $10^{-4}$ to $2 \times 10^{-2}$ mole per $dm^3$ of reactor volume, relative to the content of aluminum. In principle, however, higher concentrations are also possible. In order to combine the polymerization properties of different metallocenes, it is possible to employ mixtures of several metallocenes.

Compared with the known state of the art, the process according to the invention is distinguished by the fact that the zirconium compounds preferably used are very stable to heat in dilute solution, so that they can also be employed at temperatures up to 80° C.

The molar ratios between the polycyclic olefin and the 1-olefin employed can be varied within a wide range in the preparation of copolymers. The incorporation rate of comonomer can be controlled virtually as desired by the choice of polymerization temperature, by the concentration of the catalyst components and by the molar ratio employed. In the case of norbornene, an incorporation rate of over 40 mol % is reached.

The average molecular weight of the copolymer formed can be varied in a known manner by varying the catalyst concentration or the temperature.

The polydispersity $M_w/M_n$ of the copolymers, at values between 2.9 and 6.0 (4.5), is fairly narrow, but differs markedly from the molecular weight distributions, $M_w/M_n=2$, of the polyethylenes and polypropylenes prepared using this system. This results in a pattern of properties for the polymers which makes them particularly suitable for injection-molding.

Polymers having a viscosity number greater than 20 cm$^3$/g are formed in the copolymerization of the polycyclic olefins with the acyclic olefins, in particular with propylene. In the case of copolymers of norbornene with acyclic olefins, in particular ethylene, the glass transition temperature is above 100° C.

Polymers having a highly stereoregular structure are formed in the polymerization of cyclopentene, by virtue of the properties of the ethylene-bis-(1-indenyl)-zirconium dichloride catalyst. It must be assumed that the other polymers prepared by means of the process according to the invention also exhibit a high stereoregularity in their structure.

Amorphous copolymers can be prepared by the process described. The copolymers are transparent and hard. They are soluble, for example, in decahydronaphthalene at 135° C. and in toluene at room temperature. The polymers according to the invention can be processed by thermoplastically. No appreciable degradation or build-up of viscosity was found when they were extruded or injection-molded.

The materials according to the invention are particularly suitable for the production of extruded components, such as films or sheets, tubing, pipes, bars and fibers, and for the production of injection-molded articles of any desired shape and size. An important property of the materials according to the invention is their transparency. As a result of this, great importance attaches particularly to the optical applications of the components extruded or injection-molded from these materials. The refractive index, determined by means of an Abbé refractometer and mixed light, of the reaction products described in the examples below is within the range between 1.520 and 1.545. Since the refractive index is very near to that of crown glass (n=1.51), the products according to the invention can have various applications as a glass substitute, such as, for example, lenses, prisms, carrier plates and films for optical data memories, for video discs and for compact discs, as cover discs and focusing discs for solar cells, as cover discs and diffusing screens for objective lenses and as optical waveguides in the form of fibers or films.

The polymers according to the invention can also be employed for the preparation of polymer alloys. The alloys can be prepared in the melt or in solution. The alloys have in each case a combination of properties of the components which is advantageous for specific uses. The following polymers can be employed for alloys with the polymers according to the invention; polyethylene, polypropylene, (ethylene/propylene) copolymers, polybutylene, poly-(4-methyl-1-pentene), polyisoprene, polyisobutylene, natural rubber, poly-(methyl methacrylate), other polymethacrylates, polyacrylates, (acrylate/methacrylate) copolymers, polystyrene, (styrene/acrylonitrile) copolymers, bisphenol A polycarbonate, other polycarbonates, aromatic polyester carbonates, polyethylene terephthalate, polybutylene terephthalate, amorphous polyarylates, nylon 6, nylon 66, other polyamides, polyaramides, polyether-ketones, polyoxymethylene, polyoxyethylene, polyurethanes, polysulfones, polyether-sulfones and polyvinylidene fluoride.

The glass transition temperatures (Tg) shown in the following examples were determined by means of DSC (Differential Scanning Calorimetry) at a heating rate of 20° C./minute. The viscosity numbers shown were determined as specified in DIN 53,728.

EXAMPLE 1

Preparation of rac-Dimethylsilyl-bis-(1-indenyl)-zirconium dichloride (metallocene A)

All the following operations were carried out in an inert gas atmosphere, using absolutely dry solvents (Schlenk technique).

80 cm$^3$ (0.20 mol) of a 2.5-molar solution of n-butyllithium in hexane were added, with ice cooling, to a solution in 200 cm$^3$ of diethyl ether of 30 g (0.23 mol) of indene (technical, 91%) which had been filtered through aluminum oxide. The mixture was stirred for a further 15 minutes at room temperature and the orange solution was then added via a cannula in the course of 2 hours to a solution of 13.0 g (0.10 mol) of dimethyldichlorosilane (99%) in 30 cm$^3$ of diethyl ether. The orange suspension was stirred overnight and extracted by shaking with three times 100–150 cm$^3$ of water. The yellow organic phase was dried twice over sodium sulfate and evaporated in a rotary evaporator. The orange oil which remained was kept at 40° C. in an oil pump vacuum for 4 to hours and was freed from excess indene, in the course of which a white precipitate was deposited. A total of 20.4 g (71%) of the compound (CH$_3$)$_2$Si(Ind)$_2$ could be isolated in the form of a white to beige powder by adding 40 cm$^3$ of methanol and crystallizing at −35° C. M.p. 79–81° C. (2 diastereomers).

15.5 cm$^3$ (38.7 mmol) of a 2.5-molar solution of butyllithium in hexane were added slowly at room temperature to a solution of 5.6 g (19.4 mmol) of (CH$_3$)$_2$Si(Ind)$_2$ in 40 cm$^3$ of THF. 1 hour after the completion of the addition, the deep red solution was added dropwise in the course of 4 to 6 hours to a suspension of 7.3 g (19.4 mmol) of ZrCl$_4$.2THF in 60 cm of THF. After stirring for 2 hours, the orange precipitate was filtered off with suction on a glass frit and was recrystallized from CH$_2$Cl$_2$.1.0 g (11%) of rac-(CH$_3$)$_2$Si(Ind)$_2$ZrCl$_2$ was obtained in the form of orange crystals which gradually decompose above 200° C. The elementary analyses were correct. The EI mass spectrum gave M$^+$=448. $^1$H-NMR spectrum (CDCl$_3$): 7.04–7.60 (m, 8, arom. H), 6.90 (dd, 2, β-Ind H), 6.08 (d, 2, α-Ind H), 1.12 (s, 6, SiCH$_3$).

EXAMPLES 2-9

Metallocenes B, C, D, E, F, G, H and I as shown in Table 1 were prepared analogously to Example 1, using a dihalogeno compound as shown in Table 2 instead of the dimethyldichlorosilane and, in the case of the hafnium compounds (metallocenes G, H and I), using $HfCl_4$ instead of $ZrCl_4$.

EXAMPLE 10

Preparation of diphenylmethylene-(9-fluorenyl)-cyclopentadienyl-zirconium dichloride (metallocene L)

12.3 cm$^3$ (30.7 mmol) of a 2.5-molar solution of n-butyllithium in hexane were added slowly at room temperature to a solution of 5.10 g (30.7 mmol) of fluorene in 60 cm$^3$ of THF. After 40 minutes 7.07 g (30.7 mmol) of diphenylfulvene were added to the orange solution, and the mixture was stirred overnight. 60 cm$^3$ of water were added to the dark red solution, in the course of which the solution turned yellow, and the solution was extracted with ether. The ether phase was dried over $MgSO_4$ and concentrated and allowed to crystallize at $-35°$ C. This gave 5.1 g (42%) of 1,1-cyclopentadienyl-(9-fluorenyl)diphenylmethane as a beige powder.

2.0 g (5.0 mmol) of the compound were dissolved in 20 cm$^3$ of THF, and 6.4 cm$^3$ (10 mmol) of a 1.6-molar solution of butyllithium in hexane were added at 0° C. After stirring at room temperature for 15 minutes, the solvent was stripped off and the red residue was dried in an oil pump vacuum and washed several times with hexane. After being dried in an oil pump vacuum the red powder was added at $-78°$ C. to a suspension of 1.16 g (5.00 mmol) of $ZrCl_4$. After being warmed up slowly, the mixture was stirred for a further 2 hours at room temperature. The pink suspension was filtered through a G3 frit. The pink-red residue was washed with 20 cm$^3$ of $CH_2Cl_2$, dried in an oil pump vacuum and extracted with 120 cm$^3$ of toluene. After the solvent had been stripped off and the residue had been dried in an oil pump vacuum, 0.55 g of the zirconium complex was obtained in the form of a pink-red crystalline powder.

The orange-red filtrate from the reaction mixture was concentrated and allowed to crystallize at $-35°$ C. A further 0.45 g of the complex crystallize from $CH_2Cl_2$. Total yield 1.0 g (36%). Elementary analyses correct. The mass spectrum gave $M^+ = 556$. $^1$H-NMR spectrum (100 MHz, $CDCl_3$): 6.90-8.25 (m, 16, Flu-H, Ph-H), 6.40 (m, 2, Ph-H), 6.37 (t, 2, Cp-H), 5.80 (t, 2, Cp-H).

EXAMPLE 11

Preparation of isopropylene-(9-fluorenyl)-cyclopentadienyl-zirconium dichloride (metallocene M)

Metallocene M was prepared by a method modeled on the literature reference J. Am. Chem. Soc. 110 (1988), 6255.

EXAMPLE 12

A clean and dry 1.5 dm$^3$ polymerization reactor equipped with a stirrer was flushed with nitrogen and then with ethylene, and was charged with a solution of 25 g of norbornene in 750 cm$^3$ of toluene. The reactor was then raised to a temperature of 20° C., with stirring, and 1 bar of ethylene was injected.

20 cm$^3$ of a solution in toluene of methylaluminoxane (10.1% by weight of methylaluminoxane having a molecular weight of 1300 g/mol according to cryoscopic determination) were then metered into the reactor, and the mixture was stirred for 15 minutes at 20° C., the ethylene pressure being kept at 1 bar by further injection (saturation of the toluene with ethylene). Parallel to this, 30.5 mg of metallocene A were dissolved in 10 cm$^3$ of a toluene solution of methylaluminoxane (for concentration and quality see above) and were pre-activated by being left to stand for 15 minutes. The solution of the complex was then metered into the reactor. Polymerization was then carried out with stirring (750 r.p.m.) for 1 hour at 20° C., the ethylene pressure being kept at 1 bar by further injection. The contents of the reactor were then discharged rapidly into a stirred vessel in which 100 cm$^3$ of isopropanol had previously been placed. 2 dm$^3$ of acetone were added to this mixture, which was stirred for 10 minutes, and the suspended polymeric solid was then filtered off. The polymer which had been filtered off was then put into 300 cm$^3$ of a mixture of two parts of 3-normal hydrochloric acid and one part of ethanol, and this suspension was stirred for 2 hours. The polymer was then filtered off again, washed with water until neutral and dried for 15 hours at 80° C. and 0.2 bar. The amount of product obtained was 55 g. The viscosity number VN of the product was determined as 244 cm$^3$/g and its glass transition temperature Tg was determined as 32° C.

EXAMPLES 13-16

Polymerization tests were carried out analogously to Example 12. As compared with Example 12, the following were varied:
the nature of the metallocene employed,
the amount of metallocene employed.

All the other parameters remained constant. Table 3 shows the varied parameters and the results of the polymerizations.

EXAMPLES 17-21 and COMPARISON TESTS a and b

Polymerization tests were carried out analogously to Example 12. As compared with Example 12, the following were varied:
the nature of the metallocene employed,
the amount of metallocene employed,
the nature of the solvent for the norbornene solution,
the amount of norbornene employed,
the polymerization time (t),
the polymerization temperature (T),
the ethylene pressure (p).

All the other parameters remained constant. Table 4 shows the varied parameters and the results of the polymerizations.

EXAMPLE 22

The polymerization was carried out as in Example 12, with the exception that nitrogen was employed instead of ethylene and a mixture of 94.16 g of norbornene and 84.16 g of 4-methyl-1-pentene was employed instead of 25 g of norbornene. A further change from Example 12 was the use of 61.4 mg of metallocene A and a polymerization time of 3 hours. 3.5 g of product having a glass transition temperature of 80° C. were obtained.

EXAMPLE 23

The polymerization was carried out as in Example 12, with the exception that a mixture of 94.16 g of norbornene and 84.16 g of 4-methyl-1-pentene was employed instead of norbornene. A further change from Example 12 was the use of 62.2 m of metallocene A and a polymerization time of 3 hours. 11.8 g of product having a glass transition temperature of 55° C. were obtained.

EXAMPLE 24

A polymerization test was carried out analogously to Example 12. However, the norbornene solution charged to the reactor was a solution of 15 g of norbornene in 750 cm$^3$ of hexane; 29.6 mg of metallocene were employed. 8 g of polymer having a viscosity number of 116 cm$^3$/g and a Tg of 36° C. were obtained.

EXAMPLE 25

A clean and dry 1.5 dm$^3$ polymerization reactor equipped with a stirrer was flushed with nitrogen and then with propylene and was charged with a solution of 30 g of norbornene in 750 cm$^3$ of toluene. The reactor was then brought to a temperature of 20° C., with stirring, and 1 bar of propylene was injected. 20 cm$^3$ of a solution in toluene of methylaluminoxane (10.1% by weight of methylaluminoxane having a molecular weight of 1300 g/mol as determined by cryoscopy) were then metered into the reactor, and the mixture was stirred for 15 minutes at 20° C., the propylene pressure being maintained at 1 bar by further injection (saturation of the toluene with propylene). Parallel with this, 30.9 mg of metallocene A were dissolved in 10 cm$^3$ of a toluene solution of methylaluminoxane (for concentration and quality see above) and were pre-activated by being allowed to stand for 15 minutes. The solution of the complex was then metered into the reactor. Polymerization was then carried out for 3 hours at 20° C., with stirring (750 r.p.m.), the ethylene pressure being kept constant at 1 bar by further injection. The contents of the reactor were then discharged rapidly into a stirred vessel in which 100 cm$^3$ of isopropanol had previously been placed. 2 dm$^3$ of acetone were added to this mixture, which was stirred for 10 minutes, and the suspended polymeric solid was then filtered off.

After being filtered off, the polymer was added to 300 cm$^3$ of a mixture of two parts of 3-normal hydrochloric acid and one part of ethanol, and this suspension was stirred for 2 hours. 200 cm$^3$ of toluene were then added to the stirred mixture and, after stirring for a further 5 minutes, the toluene phase was separated off and 1 dm$^3$ of acetone was added to it. The polymer which had been dissolved in toluene by extraction of the hydrochloric acid mixture was precipitated in this way. The precipitated polymeric solid was then filtered off and dried at 80° C. and 0.2 bar for 15 hours.

The amount of product obtained was 5.4 g. The viscosity number of the product was found to be 23 cm$^3$/g and its glass transition temperature to be 96.6° C.

EXAMPLES 26-37

Polymerization tests were carried out analogously to Example 19. As compared with Example 19, the following were varied:
the nature of the metallocene employed,
the amount of metallocene employed,
the amount of norbornene employed
the polymerization temperature (T).

In Tests 28-30 a solution in toluene of methylaluminoxane containing 10.3% by weight of methylaluminoxane having a molecular weight of 750 g/mol as determined by cryoscopy was used. All the other parameters remained constant. Table 5 shows the parameters varied and the results of the polymerization.

EXAMPLE 38

A polymerization test was carried out analogously to Example 25. The norbornene solution charged to the reactor was, however, a solution of 15 g of norbornene in 750 cm$^3$ of hexane; the amount of metallocene A employed was 31.6 mg and the polymerization temperature was 40° C.

5.3 g of polymer having a viscosity number of 7 cm$^3$/g and a Tg of 87° C. were obtained.

EXAMPLE 39

A clean and dry 1.5 dm$^3$ polymerization reactor equipped with a stirrer was flushed with nitrogen and then with propylene and was charged with a solution of 107 g of norbornene in 750 cm$^3$ of toluene. The reactor was then brought to a temperature of 20° C., with stirring, and 1 bar of propylene was injected. 20 cm$^3$ of a toluene solution of methylaluminoxane (10.1% by weight of methylaluminoxane having a molecular weight of 750 g/mol as determined by cryoscopy) were then metered into the reactor, and the mixture was stirred for 15 minutes at 20° C., the propylene pressure being maintained at 1 bar by further injection (saturation of the toluene with propylene). Parallel with this, 64.1 mg of metallocene A were dissolved in 10 cm$^3$ of a toluene solution of methylaluminoxane (for concentration and quality see above), and were pre-activated by being left to stand for 15 minutes. The solution of the complex was then metered into the reactor. Polymerization was then carried out for three hours at 20° C., with stirring (750 r.p.m.), the propylene pressure being maintained at 1 bar by further injection. The contents of the reactor were then discharged rapidly into a stirred vessel in which 100 cm$^3$ of isopropanol had previously been placed. 2 dm$^3$ of acetone were added to this mixture, which was stirred for 10 minutes, and the suspended polymeric solid was then filtered off. After being filtered off, the polymer was put into 300 cm$^3$ of a mixture of two parts of 3-normal hydrochloric acid and one part of ethanol, and this suspension was stirred for 2 hours. The polymer was then filtered off again, washed with water until neutral and dried for 15 hours at 80° C. and 0.2 bar.

The amount of product obtained was 2 g. The viscosity number of the product was found to be 26.1 cm$^3$/g and its glass transition temperature to be 129.5° C.

EXAMPLES 40-43

Polymerization tests were carried out as in Example 39. Compared with Example 39, the following were varied:
the molecular weight of the methylaluminoxane,
the nature of the metallocene employed,
the amount of metallocene employed,
the amount of norbornene employed,
the propylene pressure (P).

All the other parameters remained constant: Table 6 shows the parameters varied and the results of polymerization.

EXAMPLE 44

A polymerization test was carried out as in Example 12, employing 110 g of 1,4,5,8-dimethano-1,2,3,4,4a,5,8,8a-octahydronaphthalene instead of norbornene and 61.5 mg instead of 30.5 mg of metallocene A. 17 g of polymer were obtained. The polymer was found to have a viscosity number of 120 cm³/g and a glass transition temperature of 124° C.

EXAMPLE 45

A polymerization test was carried out as in Example 17, employing a mixture of 94 g of norbornene and 68 g of cyclopentene instead of norbornene. 17.4 g of polymer were obtained. The polymer was found to have a viscosity number of 137 cm³/g and a glass transition temperature of 117° C.

EXAMPLE 46

Two ethylene/norbornene copolymers according to the invention, having glass transition temperatures of 55 and 115° C., respectively, and viscosity numbers of 240 and 230 cm³/g, respectively, were found to have norbornene incorporation rates of 27 and 41.5 mol %, respectively, by means of $C^{13}$-NMR (Nuclear Magnetic Resonance) based on the ratio between the number of tertiary and secondary carbon atoms.

EXAMPLE 47

40 g of a polymer prepared as in Example 20 were kneaded under an inert gas (Ar) at 200° C. for 1 hour in a measuring kneader (made by HAAKE). The torque had stabilized after charging and remained constant over a period of 45 minutes.

EXAMPLE 48

Analogously to Example 46, 20 g of a polymer prepared as in Example 20 were kneaded together with 20 g of a polymer prepared as in Example 21. The alloy thus obtained was transparent. Only one glass stage at 149° C. could be found by means of DSC at a heating rate of 20° C./minute.

TABLE 1

| Compound | Brief description |
|---|---|
| rac-Dimethylsilyl-bis-(1-indenyl)-zirconium dichloride | Metallocene A |
| rac-Dimethylgermyl-bis-(1-indenyl)-zirconium dichloride | Metallocene B |
| rac-Phenylmethylsilyl-bis-(1-indenyl)-zirconium dichloride | Metallocene C |
| rac-Phenylvinylsilyl-bis-(1-indenyl)-zirconium dichloride | Metallocene D |
| 1-Silacyclobutyl-bis-(1'-indenyl)-zirconium dichloride (Mixture of isomers: 57% of rac-Isomer and 43% of meso-isomer) | Metallocene E |
| rac-Ethylene-bis-(1-indenyl)-zirconium dichloride | Metallocene F |
| rac-Diphenylsilyl-bis-(1-indenyl)-hafnium dichloride | Metallocene G |
| rac-Phenylmethylsilyl-bis-(1-indenyl)-hafnium dichloride | Metallocene H |
| rac-Dimethylsilyl-bis-(1-indenyl)-hafnium dichloride | Metallocene I |
| rac-Diphenylsilyl-bis-(1-indenyl)-zirconium dichloride | Metallocene K |
| Diphenylmethylene-(9-fluorenyl)-cyclopentadienyl-zirconium dichloride | Metallocene L |
| Isopropylene-(9-fluorenyl)-cyclopentadienyl-zirconium dichloride | Metallocene M |

TABLE 2

| Metallocene | Dihalogeno compound |
|---|---|
| A | Dimethyldichlorosilane |
| B | Dimethylgermanium dichloride (Dimethyldichlorogermane) |
| C | Phenylmethyldichlorosilane |
| D | Phenylvinyldichlorosilane |
| E | Cyclotrimethylenedichlorosilane |
| F | 1,2-Dibromoethane |
| G | Diphenyldichlorosilane |
| H | Phenylmethyldichlorosilane |
| I | Dimethyldichlorosilane |
| J | Diphenyldichlorosilane |

TABLE 3

| Example | Metallocene | Amount of metallocene (mg) | T (°C.) | Amount of product (g) | Viscosity number (cm³/g) | Tg (DSC) (°C.) |
|---|---|---|---|---|---|---|
| 13 | B | 31.4 | 20 | 3.3 | 337 | 23.5 |
| 14 | K | 33.5 | 20 | 14.0 | 96 | 31.2 |
| 15 | L | 43.7 | 20 | 9.0 | 121 | 37.6 |
| 16 | M | 29.3 | 20 | 12.0 | 99 | 32.2 |

TABLE 4

| Example | Metallocene | Amount of metallocene (mg) | Amount of norbornene (g) | T (°C.) | P (bar) | t (h) | Solvent | Amount of product (g) | Viscosity number (cm³/g) | Tg (DSC) (°C.) |
|---|---|---|---|---|---|---|---|---|---|---|
| 17 | A | 60 | 107 | 20 | 1 | 3 | toluene | 54.1 | 177 | 105 |
| 18 | A | 66.5 | 214 | 70 | 1.5 | 3 | petroleum ether fraction b.p. 110–130° C. | 9.5 | 55 | 163 |
| 19 | A | 60 | 107 | 40 | 1 | 3 | toluene | 6.0 | 62 | 156 |
| 20 | A | 60 | 180 | 20 | 1 | 1 | toluene | 7.6 | 65 | 146 |
| Comp. test a | F | 60 | 180 | 20 | 1 | 1 | toluene | 35.0 | 157 | 134 |
| 21 | A | 60 | 214 | 20 | 1 | 3 | toluene | 16.8 | 110 | 154 |
| Comp. test b | F | 60 | 214 | 20 | 1 | 3 | toluene | 34.4 | 191 | 141 |

TABLE 5

| Example | Metal-locene | Amount of metal-locene (mg) | Amount of nor-bornene (g) | T (°C.) | Amount of product (g) | Viscosity number (cm³/g) | Tg (DSC) (°C.) |
|---|---|---|---|---|---|---|---|
| 26 | C | 60.9 | 30 | 40 | 1.4 | 19 | 91.1 |
| 27 | D | 51.6 | 30 | 40 | 1.5 | 22 | 89.7 |
| 28 | E | 56.2 | 30 | 40 | 1.1 | 22 | 103.6 |
| 29 | K | 38.0 | 30 | 40 | 2.0 | 14 | 91.8 |
| 30 | G | 351.0 | 30 | 70 | 1.2 | 30 | 50.0 |
| 31 | H | 100.2 | 40 | 70 | 1.1 | 26 | 48.2 |
| 32 | I | 177.0 | 30 | 40 | 3.0 | 24 | 61.0 |
| 33 | I | 302.0 | 30 | 50 | 7.0 | 4 | 70.4 |
| 34 | L | 30.6 | 30 | 20 | 50.0 | 14 | 26.5 |
| 35 | L | 30.1 | 40 | 40 | 110.0 | 27 | 23.7 |
| 36 | L | 15.0 | 40 | 50 | 23.0 | 4 | 62.0 |
| 37 | M | 30.3 | 80 | 20 | 1.3 | 22 | 26.6 |

TABLE 6

| Example | Metal-locene | Amount of metal-locene (mg) | Amount of nor-bornene (g) | Pressure (bar) | Mw (MAO) (g/mol) | Amount of product (g) | Viscosity number (cm³/g) | Tg (DSC) (°C.) |
|---|---|---|---|---|---|---|---|---|
| 40 | A | 89 | 107 | 3 | 750 | 3.1 | 31 | 107 |
| 41 | A | 60 | 50 | 1–3* | 750 | 5.2 | 25.6 | 101 |
| 42 | A | 60 | 107 | 1–3* | 1300 | 5.3 | 21.0 | 120 |
| 43 | F | 60 | 107 | 1–3* | 1300 | 12.0 | 20.0 | 129 |

*The pressure was increased during the polymerization in the course of 1 hour from 1 to 3 bar at a linear rate.

We claim:

1. A process for the preparation of a cycloolefin polymer by polymerizing 0.1 to 100% by weight, relative to the total amount of the monomers, of at least one monomer of the formulae I, II, III or IV

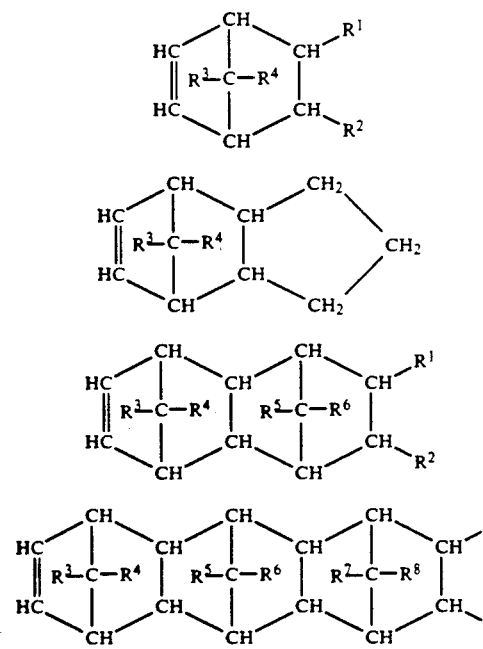

in which $R^1$, $R^2$, $R^3$, $R^4$, $R^5$, $R^6$, $R^7$ and $R^8$ are identical or different and denote a hydrogen atom or a $C_1$-$C_8$-alkyl radical, it being possible for identical radicals in the various formulae to have a different meaning. 0 to 99.9% by weight, relative to the total amount of the monomers, of a cycloolefin of the formula V

in which n is a number from 2 to 10, and 0 to 99.9% by weight, relative to the total amount of the monomers, of at least one acyclic 1-olefin of the formula VI

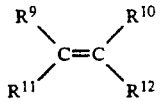

in which $R^9$, $R^{10}$, $R^{11}$ and $R^{12}$ are identical or different and denote a hydrogen atom or a $C_1$-$C_8$-alkyl radical, in solution, in suspension, in a monomer melt or in the gas phase, at a temperature of $-78°$ to $150°$ C., under a pressure of 0.5 to 64 bar, and in the presence of a catalyst which is composed of a metallocene as the transition metal component and an aluminoxane of the formula VII

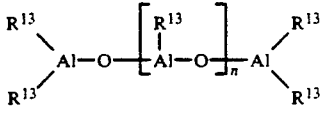

for the linear type, and/or of the formula VIII

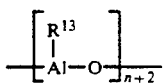

for the cyclic type, $R^{13}$ in the formulae VII and VIII denoting a $C_1$-$C_6$-alkyl group or phenyl or benzyl and n being an integer from 2 to 50, which comprises carrying out the polymerization in the presence of a catalyst the transition metal component of which is a compound of the formula IX

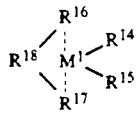 (IX)

in which
- $M^1$ is titanium, zirconium, hafnium, vanadium, niobium or tantalum,
- $R^{14}$ and $R^{15}$ are identical or different and denote a hydrogen atom, a halogen atom, a $C_1$-$C_{10}$-alkyl group, a $C_1$-$C_{10}$-alkoxy group, a $C_6$-$C_{10}$-aryl group, a $C_6$-$C_{10}$-aryloxy group, a $C_2$-$C_{10}$-alkenyl group, a $C_7$-$C_{40}$-arylalkyl group, a $C_7$-$C_{40}$-alkylaryl group or a $C_8$-$C_{40}$-arylalkenyl group,
- $R^{16}$ and $R^{17}$ are identical or different and denote a mononuclear or polynuclear hydrocarbon radical which can form a sandwich structure together with the central atom $M^1$,
- $R^{18}$ is

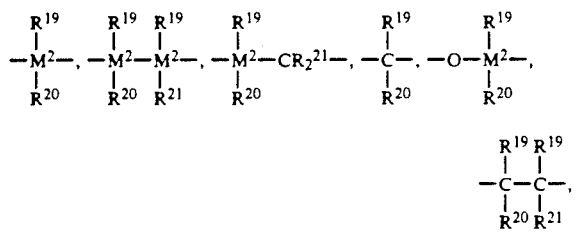

$=BR^{19}$, $=AlR^{19}$, $—Ge—$, $—Sn—$, $—O—$, $—S—$, $=SO$, $=SO_2$, $=NR^{19}$, $=CO$, $=PR^{19}$ or $=P(O)R^{19}$; $R^{19}$, $R^{20}$ and $R^{21}$ being identical or different and denoting a hydrogen atom, a halogen atom, a $C_1$-$C_{10}$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-alkoxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group or $R^{19}$ and $R^{20}$ or $R^{19}$ and $R^{21}$, in each case with the atoms linking them, forming a ring, provided that when $R^{16}$ and $R^{17}$ are identical and $R^{18}$ is

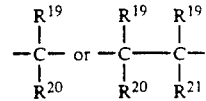

$R^{19}$ and $R^{20}$ are not hydrogen or $C_1$-$C_{10}$-alkyl; and $M^2$ is silicon, germanium or tin.

2. The process as claimed in claim 1, wherein the metallocene used is
rac-dimethylsilyl-bis-(1-indenyl)-zirconium dichloride,
rac-dimethylgermyl-bis-(1-indenyl)-zirconium dichloride,
rac-phenylmethylsilyl-bis-(1-indenyl)-zirconium dichloride,
rac-phenylvinylsilyl-bis-(1-indenyl)-zirconium dichloride,
1-silacyclobutylsilyl-bis-(1'-indenyl)-hafnium dichloride,
rac-diphenylsilyl-bis-(1-indenyl)-hafnium dichoride,
rac-phenylmethylsilyl-bis-(1-indenyl)-hafnium dichloride,
rac-dimethylsilyl-bis-(1-indenyl)-hafnium dichloride,
rac-diphenylsilyl-bis-(1-indenyl)-zirconium dichloride,
diphenylmethylene-(9-fluorenyl)-cyclopentadienyl-zirconium dichloride or
isopropylene-(9-fluorenyl)-cyclopentadienyl-zirconium dichloride.

3. The process as claimed in claim 1, wherein the polycyclic olefin is dimethano-octahydronaphthalene and the 1-olefin is ethylene.

4. The process as claimed in claim 1, wherein the polycyclic olefin is dimethano-octahydronapththalene and the 1-olefin is propylene.

5. The process as claimed in claim 1, wherein the polycyclic olefin is norbornene and the 1-olefin is ethylene.

6. The process as claimed in claim 1, wherein the polycyclic olefin is norbornene and the 1-olefin is propylene.

* * * * *